US005168048A

United States Patent [19]

Quax

[11] Patent Number: 5,168,048

[45] Date of Patent: Dec. 1, 1992

[54] PENICILLIN G ACYLASE, A GENE ENCODING THE SAME AND A METHOD FOR THE PRODUCTION OF THIS ENZYME

[75] Inventor: Wilhelmus J. Quax, Voorschoten, Netherlands

[73] Assignee: Gist-brocades NV, Delft, Netherlands

[21] Appl. No.: 687,400

[22] Filed: Apr. 18, 1991

[30] Foreign Application Priority Data

Apr. 18, 1990 [EP] European Pat. Off. ........ 90200962.0
Dec. 20, 1990 [EP] European Pat. Off. ........ 90203463.6

[51] Int. Cl.[5] ........................ C12P 21/02; C12N 1/21; C12N 15/09; C07H 21/04

[52] U.S. Cl. ................................ 435/69.1; 435/252.3; 435/252.33; 435/320.1; 435/829; 435/230; 536/27; 935/72; 935/73

[58] Field of Search .................. 435/230, 320.1, 252.3, 435/252.33, 69.1, 829; 536/27

[56] References Cited

FOREIGN PATENT DOCUMENTS 0107823 5/1984 European Pat. Off. .
0336446 10/1989 European Pat. Off. .

*Primary Examiner*—Robert A. Wax
*Assistant Examiner*—Gabriele E. Bugaisky
*Attorney, Agent, or Firm*—Barbara Rae-Venter

[57] ABSTRACT

The invention provides a gene encoding penicillin G acylase, the enzyme encoded by said gene and a method for the production of said enzyme by incorporating said gene in a host and bringing the same to expression. The gene is preferably obtained from a strain of the microorganism *Alcaligenes faecalis.*

14 Claims, 8 Drawing Sheets tac-P (124 bps)

SEQUENCE LISTING (1) GENERAL INFORMATION:
  (i) APPLICANT: Quax, Wilhelmus J.
  (ii) TITLE OF INVENTION: Penicillin G Acylase, a Gene Encoding the Same and a Method for the Production of This Enzyme
  (iii) NUMBER OF SEQUENCES: 8
  (iv) CORRESPONDENCE ADDRESS:
    (A) ADDRESSEE: Cooley Godward Castro Huddleson & Tatum
    (B) STREET: Five Palo Alto Square
    (C) CITY: Palo Alto
    (D) STATE: CA
    (E) COUNTRY: USA
    (F) ZIP: 94306
  (v) COMPUTER READABLE FORM:
    (A) MEDIUM TYPE: Floppy disc
    (B) COMPUTER: IBM PC compatible
    (C) OPERATING SYSTEM: PC-DOS/MS-DOS
    (D) SOFTWARE: WordPerfect 5.0
  (vi) CURRENT APPLICATION DATA:
    (A) APPLICATION NUMBER: 07/687,400
    (B) FILING DATE: April 18, 1991
    (C) CLASSIFICATION:
  (viii) ATTORNEY/AGENT INFORMATION:
    (A) NAME: Rae-Venter Ph.D., Barbara .
    (B) REGISTRATION NUMBER: 32750
    (C) REFERENCE/DOCKET NUMBER: GBR0-028/00US
  (ix) TELECOMMUNICATION INFORMATION:
    (A) TELEPHONE: 415-494-7622
    (B) TELEFAX: 415-857-0663
(2) INFORMATION FOR SEQ ID NO:1:
  (i) SEQUENCE CHARACTERISTICS:
    (A) LENGTH: 2451 base pairs
    (B) TYPE: nucleic acid
    (C) STRANDEDNESS: single
    (D) TOPOLOGY: linear
  (ii) MOLECULE TYPE: DNA (genomic)
  (iii) HYPOTHETICAL: NO
  (iv) ANTI-SENSE: NO
  (vi) ORIGINAL SOURCE:
    (A) ORGANISM: *Alcaligenes faecalis*
  (ix) FEATURE:
    (A) NAME/KEY: CDS
    (B) LOACTION: 1..2451
    (D) OTHER INFORMATION: /function= "enzyme" /product= "penicillin acylase or penicillin amidase"
  (xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | CAG | AAA | GGG | CTT | GTT | CGT | ACC | GGG | CTT | GTG | GCC | GCT | GGT | TTG | ATC | 48 |
| Met | Gln | Lys | Gly | Leu | Val | Arg | Thr | Gly | Leu | Val | Ala | Ala | Gly | Leu | Ile | |
| 1 | | | | 5 | | | | | 10 | | | | | 15 | | |
| TTG | GGT | TGG | GCG | GGG | GCA | CCG | ACC | CAC | GCG | CAA | GTG | CAG | TCG | GTA | GAG | 96 |
| Leu | Gly | Trp | Ala | Gly | Ala | Pro | Thr | His | Ala | Gln | Val | Gln | Ser | Val | Glu | |
| | | | 20 | | | | | 25 | | | | | 30 | | | |
| GTG | ATG | CGG | GAC | AGT | TAT | GGC | GTG | CCG | CAC | GTC | TTT | GCC | GAC | AGC | CAC | 144 |

-continued

SEQUENCE LISTING

| | | | | | | | | | | | | | | | | |
|---|---|---|---|---|---|---|---|---|---|---|---|---|---|---|---|---|
| Val | Met | Arg | Asp | Ser | Tyr | Gly | Val | Pro | His | Val | Phe | Ala | Asp | Ser | His | |
| | | 35 | | | | | 40 | | | | | 45 | | | | |
| TAT | GGC | TTG | TAT | TAC | GGC | TAT | GGT | TAT | GCG | GTC | GCC | CAA | GAC | CGT | CTG | 192 |
| Tyr | Gly | Leu | Tyr | Tyr | Gly | Tyr | Gly | Tyr | Ala | Val | Ala | Gln | Asp | Arg | Leu | |
| | 50 | | | | | 55 | | | | | 60 | | | | | |
| TTC | CAG | ATG | GAC | ATG | GCG | CGT | CGC | TCC | TTT | GTC | GGC | ACA | ACC | GCC | GCC | 240 |
| Phe | Gln | Met | Asp | Met | Ala | Arg | Arg | Ser | Phe | Val | Gly | Thr | Thr | Ala | Ala | |
| 65 | | | | | 70 | | | | | 75 | | | | | 80 | |
| GTC | TTA | GGC | CCT | GGT | GAG | CAA | GAT | GCC | TAC | GTC | AAG | TAC | GAC | ATG | CAG | 288 |
| Val | Leu | Gly | Pro | Gly | Glu | Gln | Asp | Ala | Tyr | Val | Lys | Tyr | Asp | Met | Gln | |
| | | | | 85 | | | | | 90 | | | | | 95 | | |
| GTG | CGG | CAG | AAC | TTC | ACC | CCG | GCT | TCC | ATA | CAG | CGG | CAG | ATC | GCG | GCC | 336 |
| Val | Arg | Gln | Asn | Phe | Thr | Pro | Ala | Ser | Ile | Gln | Arg | Gln | Ile | Ala | Ala | |
| | | | 100 | | | | | 105 | | | | | 110 | | | |
| TTG | TCC | AAG | GAT | GAG | CGC | GAT | ATT | TTT | CGT | GGC | TAT | GCC | GAT | GGC | TAT | 384 |
| Leu | Ser | Lys | Asp | Glu | Arg | Asp | Ile | Phe | Arg | Gly | Tyr | Ala | Asp | Gly | Tyr | |
| | | 115 | | | | | 120 | | | | | 125 | | | | |
| AAC | GCC | TAT | CTG | GAG | CAG | GTG | CGG | CGT | CGC | CCT | GAG | TTG | CTG | CCC | AAA | 432 |
| Asn | Ala | Tyr | Leu | Glu | Gln | Val | Arg | Arg | Arg | Pro | Glu | Leu | Leu | Pro | Lys | |
| | 130 | | | | | 135 | | | | | 140 | | | | | |
| GAA | TAT | GTG | GAT | TTT | GAT | TTC | CAG | CCC | GAG | CCG | CTG | ACC | GAC | TTT | GAT | 480 |
| Glu | Tyr | Val | Asp | Phe | Asp | Phe | Gln | Pro | Glu | Pro | Leu | Thr | Asp | Phe | Asp | |
| 145 | | | | | 150 | | | | | 155 | | | | | 160 | |
| GTG | GTC | ATG | ATC | TGG | GTG | GGC | TCC | ATG | GCC | AAT | CGC | TTC | TCC | GAC | ACG | 528 |
| Val | Val | Met | Ile | Trp | Val | Gly | Ser | Met | Ala | Asn | Arg | Phe | Ser | Asp | Thr | |
| | | | | 165 | | | | | 170 | | | | | 175 | | |
| AAT | CTG | GAA | GTG | ACG | GCA | CTG | GCC | ATG | CGT | CAG | TCT | CTG | GAG | AAA | CAG | 576 |
| Asn | Leu | Glu | Val | Thr | Ala | Leu | Ala | Met | Arg | Gln | Ser | Leu | Glu | Lys | Gln | |
| | | | 180 | | | | | 185 | | | | | 190 | | | |
| CAC | GGC | CCG | GAA | CGA | GGC | CGT | GCC | TTG | TTT | GAT | GAG | CTG | CTG | TGG | ATC | 624 |
| His | Gly | Pro | Glu | Arg | Gly | Arg | Ala | Leu | Phe | Asp | Glu | Leu | Leu | Trp | Ile | |
| | | 195 | | | | | 200 | | | | | 205 | | | | |
| AAT | GAC | ACA | ACA | GCT | CCC | ACT | ACG | GTT | CCG | GCC | CCC | GCT | GCC | GAG | CAC | 672 |
| Asn | Asp | Thr | Thr | Ala | Pro | Thr | Thr | Val | Pro | Ala | Pro | Ala | Ala | Glu | His | |
| | 210 | | | | | 215 | | | | | 220 | | | | | |
| AAG | CCG | CAG | GCA | CAA | GCA | GGG | ACG | CAG | GAT | CTG | GCT | CAT | GTT | TCC | TCG | 720 |
| Lys | Pro | Gln | Ala | Gln | Ala | GLy | Thr | Gln | Asp | Leu | Ala | His | Val | Ser | Ser | |
| 225 | | | | | 230 | | | | | 235 | | | | | 240 | |
| CCA | GTA | CTG | GCT | ACC | GAG | CTA | GAG | CGC | CAG | GAC | AAG | CAC | TGG | GGC | GGC | 768 |
| Pro | Val | Leu | Ala | Thr | Glu | Leu | Glu | Arg | Gln | Asp | Lys | His | Trp | Gly | Gly | |
| | | | | 245 | | | | | 250 | | | | | 255 | | |
| CGT | GGC | CCG | GAC | TTC | GCG | CCC | AAG | GCT | AGC | AAC | CTG | TGG | AGC | ACT | CGC | 816 |
| Arg | Gly | Pro | Asp | Phe | Ala | Pro | Lys | Ala | Ser | Asn | Leu | Trp | Ser | Thr | Arg | |
| | | | 260 | | | | | 265 | | | | | 270 | | | |
| CCC | GAG | CGA | GTG | CAG | GAG | GGC | TCG | ACC | GTA | CTG | ATC | AAC | GGC | CCA | CAG | 864 |
| Pro | Glu | Arg | Val | Gln | Glu | Gly | Ser | Thr | Val | Leu | Ile | Asn | Gly | Pro | Gln | |
| | | 275 | | | | | 280 | | | | | 285 | | | | |
| TTT | GGC | TGG | TAC | AAC | CCG | GCC | TAC | ACC | TAT | GGC | ATT | GGC | TTG | CAT | GGC | 912 |
| Phe | Gly | Trp | Tyr | Asn | Pro | Ala | Tyr | Thr | Tyr | Gly | Ile | Gly | Leu | His | Gly | |
| | 290 | | | | | 295 | | | | | 300 | | | | | |
| GCC | GGC | TTC | GAT | GTG | GTG | GGT | AAT | ACG | CCT | TTT | GCC | TAT | CCG | ATC | GTA | 960 |
| Ala | Gly | Phe | Asp | Val | Val | Gly | Asn | Thr | Pro | Phe | Ala | Tyr | Pro | Ile | Val | |

-continued

SEQUENCE LISTING

| | | | | | | | | | | | | | | | | |
|---|---|---|---|---|---|---|---|---|---|---|---|---|---|---|---|---|
| 305 | | | | | 310 | | | | | 315 | | | | | 320 | |
| CTG | TTT | GGC | ACC | AAT | AGC | GAG | ATT | GCC | TGG | GGG | GCG | ACT | GCT | GGC | CCG | 1008 |
| Leu | Phe | Gly | Thr | Asn | Ser | Glu | Ile | Ala | Trp | Gly | Ala | Thr | Ala | Gly | Pro | |
| | | | | 325 | | | | | 330 | | | | | 335 | | |
| CAA | GAT | GTG | GTG | GAC | ATA | TAT | CAG | GAA | AAA | TTG | AAC | CCC | TCG | CGT | GCC | 1056 |
| Gln | Asp | Val | Val | Asp | Ile | Tyr | Gln | Glu | Lys | Leu | Asn | Pro | Ser | Arg | Ala | |
| | | | 340 | | | | | 345 | | | | | 350 | | | |
| GAT | CAG | TAC | TGG | TTC | AAC | AAT | GCC | TGG | CGC | ACG | ATG | GAG | CAG | CGC | AAG | 1104 |
| Asp | Gln | Tyr | Trp | Phe | Asn | Asn | Ala | Trp | Arg | Thr | Met | Glu | Gln | Arg | Lys | |
| | | 355 | | | | | 360 | | | | | 365 | | | | |
| GAA | CGT | ATC | CAG | GTA | CGC | GGT | CAG | GCT | GAT | CGG | GAA | ATG | ACG | ATC | TGG | 1152 |
| Glu | Arg | Ile | Gln | Val | Arg | Gly | Gln | Ala | Asp | Arg | Glu | Met | Thr | Ile | Trp | |
| | 370 | | | | | 375 | | | | | 380 | | | | | |
| CGC | ACC | GTG | CAC | GGC | CCT | GTG | ATG | CAG | TTT | GAT | TAC | GAT | CAG | GGC | GCG | 1200 |
| Arg | Thr | Val | His | Gly | Pro | Val | Met | Gln | Phe | Asp | Tyr | Asp | Gln | Gly | Ala | |
| 385 | | | | 390 | | | | | 395 | | | | | 400 | | |
| GCG | TAC | AGC | AAG | AAA | CGC | AGC | TGG | GAT | GGC | TAT | GAG | GTG | CAG | TCC | TTG | 1248 |
| Ala | Tyr | Ser | Lys | Lys | Arg | Ser | Trp | Asp | Gly | Tyr | Glu | Val | Gln | Ser | Leu | |
| | | | | 405 | | | | | 410 | | | | | 415 | | |
| GAT | CAA | GCC | AGC | AAG | ATG | GCG | ATT | TCG | ATC | AAC | TGG | TAC | TAC | GCC | GAC | 1344 |
| Asp | Gln | Ala | Ser | Lys | Met | Ala | Ile | Ser | Ile | Asn | Trp | Tyr | Tyr | Ala | Asp | |
| | | 435 | | | | | 440 | | | | | 445 | | | | |
| AAG | CAC | GGC | AAT | ATT | GGT | TAT | GTC | TCG | CCG | GCC | TTC | CTG | CCC | CAG | CGT | 1392 |
| Lys | His | Gly | Asn | Ile | Gly | Tyr | Val | Ser | Pro | Ala | Phe | Leu | Pro | Gln | Arg | |
| | 450 | | | | | 455 | | | | | 460 | | | | | |
| CCT | GCC | GAT | CAG | GAC | ATC | CGT | GTC | CCT | GCC | AAG | GGG | GAT | GGC | AGC | ATG | 1440 |
| Pro | Ala | Asp | Gln | Asp | Ile | Arg | Val | Pro | Ala | Lys | Gly | Asp | Gly | Ser | Met | |
| 465 | | | | | 470 | | | | | 475 | | | | | 480 | |
| GAG | TGG | CTG | GGC | ATC | AAG | AGT | TTC | GAC | GCG | ATT | CCC | AAA | GCC | TAC | AAT | 1488 |
| Glu | Trp | Leu | Gly | Ile | Lys | Ser | Phe | Asp | Ala | Ile | Pro | Lys | Ala | Tyr | Asn | |
| | | | | 485 | | | | | 490 | | | | | 495 | | |
| CCA | CCC | CAG | GGC | TAT | CTG | GTC | AAC | TGG | AAC | AAC | AAG | CCT | GCG | CCG | GAC | 1536 |
| Pro | Pro | Gln | Gly | Tyr | Leu | Val | Asn | Trp | Asn | Asn | Lys | Pro | Ala | Pro | Asp | |
| | | | 500 | | | | | 505 | | | | | 510 | | | |
| AAA | ACC | AAT | ACG | GAT | ACT | TAC | TAT | TGG | ACC | TAT | GGC | GAC | CGC | ATG | AAT | 1584 |
| Lys | Thr | Asn | Thr | Asp | Thr | Tyr | Tyr | Trp | Thr | Tyr | Gly | Asp | Arg | Met | Asn | |
| | | 515 | | | | | 520 | | | | | 525 | | | | |
| GAA | CTG | GTC | AGT | CAG | TAC | CAG | CAG | AAA | GAC | CTC | TTC | AGT | GTG | CAG | GAG | 1632 |
| Glu | Leu | Val | Ser | Gln | Tyr | Gln | Gln | Lys | Asp | Leu | Phe | Ser | Val | Gln | Glu | |
| | 530 | | | | | 535 | | | | | 540 | | | | | |
| ATC | TGG | GAG | TTC | AAT | CAA | AAA | GCC | TCC | TAT | AGC | GAT | GTG | AAC | TGG | CGC | 1680 |
| Ile | Trp | Glu | Phe | Asn | Gln | Lys | Ala | Ser | Tyr | Ser | Asp | Val | Asn | Trp | Arg | |
| 545 | | | | | 550 | | | | | 555 | | | | | 560 | |
| TAC | TTC | CGC | CCA | CAT | CTG | GAA | AAG | CTG | GCG | CAA | CAG | CTG | CCG | GCC | GAC | 1728 |
| Tyr | Phe | Arg | Pro | His | Leu | Glu | Lys | Leu | Ala | Gln | Gln | Leu | Pro | Ala | Asp | |
| | | | | 565 | | | | | 570 | | | | | 575 | | |
| GAT | AGC | AGC | AAG | GCG | GCG | CTG | ACG | ATG | TTG | CTC | GCC | TGG | GAT | GGA | ATG | 1776 |
| Asp | Ser | Ser | Lys | Ala | Ala | Leu | Thr | Met | Leu | Leu | Ala | Trp | Asp | Gly | Met | |
| | | | 580 | | | | | 585 | | | | | 590 | | | |
| GAA | CAG | GAT | CAG | GGA | GGG | CAA | AAT | GCC | GGA | CCG | GCG | CGG | GTG | CTC | TTC | 1824 |
| Glu | Gln | Asp | Gln | Gly | Gly | Gln | Asn | Ala | Gly | Pro | Ala | Arg | Val | Leu | Phe | |
| | | 595 | | | | | 600 | | | | | 605 | | | | |

-continued

| SEQUENCE LISTING | | | | | | | | | | | | | | | | |
|---|---|---|---|---|---|---|---|---|---|---|---|---|---|---|---|---|
| AAG | ACC | TGG | CTG | GAA | GAA | ATG | TAC | AAG | CAG | GTC | TTG | ATG | CCG | GTG | GTG | 1872 |
| Lys | Thr | Trp | Leu | Glu | Glu | Met | Tyr | Lys | Gln | Val | Leu | Met | Pro | Val | Val | |
| | 610 | | | | | 615 | | | | | 620 | | | | | |
| CCT | GAA | TCG | CAT | CGC | GCC | ATG | TAT | AGC | CAG | ACT | GGT | TTT | GCC | ACG | CAG | 1920 |
| Pro | Glu | Ser | His | Arg | Ala | Met | Tyr | Ser | Gln | Thr | Gly | Phe | Ala | Thr | Gln | |
| 625 | | | | | 630 | | | | | 635 | | | | | 640 | |
| CAA | GGT | CCC | AAC | CCC | GGT | TCC | ATC | AAC | TTG | AGC | ATG | GGC | ACC | AAG | GTC | 1968 |
| Gln | Gly | Pro | Asn | Pro | Gly | Ser | Ile | Asn | Leu | Ser | Met | Gly | Thr | Lys | Val | |
| | | | | 645 | | | | | 650 | | | | | 655 | | |
| TTG | TTG | CGT | GCC | TTG | GTG | CTG | GAA | GCC | CAT | CCC | GAT | CCC | AAG | CGT | GTG | 2016 |
| Leu | Leu | Arg | Ala | Leu | Val | Leu | Glu | Ala | His | Pro | Asp | Pro | Lys | Arg | Val | |
| | | | 660 | | | | | 665 | | | | | 670 | | | |
| AAT | GTC | TTT | GGT | GAG | CGT | TCG | TCT | CAG | GAA | ATC | ATG | CAC | ACA | GCT | TTG | 2064 |
| Asn | Val | Phe | Gly | Glu | Arg | Ser | Ser | Gln | Glu | Ile | Met | His | Thr | Ala | Leu | |
| | | 675 | | | | | 680 | | | | | 685 | | | | |
| CAA | AAT | GCG | CAG | GCC | CGC | TTG | AGC | CAG | GAG | CAG | GGC | GCT | CAG | ATG | GCG | 2112 |
| Gln | Asn | Ala | Gln | Ala | Arg | Leu | Ser | Gln | Glu | Gln | Gly | Ala | Gln | Met | Ala | |
| | 690 | | | | | 695 | | | | | 700 | | | | | |
| CGC | TGG | ACC | ATG | CCG | ACC | TCC | GTG | CAT | CGT | TTC | AGC | GAC | AAG | AAC | TTC | 2160 |
| Arg | Trp | Thr | Met | Pro | Thr | Ser | Val | His | Arg | Phe | Ser | Asp | Lys | Asn | Phe | |
| 705 | | | | | 710 | | | | | 715 | | | | | 720 | |
| ACG | GGA | ACC | CCG | CAG | ACG | ATG | CCT | GGC | AAT | ACC | TTT | GCC | TTT | ACC | GGC | 2208 |
| Thr | Gly | Thr | Pro | Gln | Thr | Met | Pro | Gly | Asn | Thr | Phe | Ala | Phe | Thr | Gly | |
| | | | | 725 | | | | | 730 | | | | | 735 | | |
| TAT | CAG | AAT | CGA | GGC | ACG | GAA | AAT | AAC | CGC | GTG | GTG | TTT | GAT | GCC | AAG | 2256 |
| Tyr | Gln | Asn | Arg | Gly | Thr | Glu | Asn | Asn | Arg | Val | Val | Phe | Asp | Ala | Lys | |
| | | | 740 | | | | | 745 | | | | | 750 | | | |
| GGC | GTG | GAG | TTC | TGC | GAC | GCC | ATG | CCG | CCC | GGC | CAA | AGC | GGT | TTC | ACC | 2304 |
| Gly | Val | Glu | Phe | Cys | Asp | Ala | Met | Pro | Pro | Gly | Gln | Ser | Gly | Phe | Thr | |
| | | 755 | | | | | 760 | | | | | 765 | | | | |
| GAC | CGC | AAT | GGA | GTG | CGC | AGC | CCG | CAT | TAT | GAG | GAT | CAG | CTG | AAG | TTG | 2352 |
| Asp | Arg | Asn | Gly | Val | Arg | Ser | Pro | His | Tyr | Glu | Asp | Gln | Leu | Lys | Leu | |
| | 770 | | | | | 775 | | | | | 780 | | | | | |
| TAC | GAG | AAC | TTC | GAG | TGC | AAG | ACG | ATG | GAT | GTG | ACG | CAT | GCG | GAC | ATT | 2400 |
| Tyr | Glu | Asn | Phe | Glu | Cys | Lys | Thr | Met | Asp | Val | Thr | His | Ala | Asp | Ile | |
| 785 | | | | | 790 | | | | | 795 | | | | | 800 | |
| CGT | CGT | AAT | GCG | CAA | AGC | AGC | ACG | ATG | CTG | TTG | ATT | CAG | CCT | CAG | CCT | 2448 |
| Arg | Arg | Asn | Ala | Gln | Ser | Ser | Thr | Met | Leu | Leu | Ile | Gln | Pro | Gln | Pro | |
| | | | | 805 | | | | | 810 | | | | | 815 | | |
| TAA | | | | | | | | | | | | | | | | 2451 |
| End | | | | | | | | | | | | | | | | |

(2) INFORMATION SEQ ID NO:2:
(i) SEQUENCE CHARACTERISTICS:
(A) LENGTH: 124 base pairs
(B) TYPE: nucleic acid
(C) STRANDEDNESS: single
(D) TOPOLOGY: linear
(ii) MOLECULE TYPE: DNA (synthetic)
(iii) HYPOTHETICAL: NO
(iv) ANTI-SENSE: NO
(vi) ORIGINAL SOURCE:
(A) ORGANISM: *E. coli*

-continued

SEQUENCE LISTING (ix) FEATURE:
(A) NAME/KEY: TAC PROMOTER
(B) LOCATION: 1..124
(D) OTHER INFORMATION: bp 35-40 = "−35" region
bp 57-62 = "−10" region
bp 110-114 = Shine Dalgarno lac gene (xi) SEQUENCE DESCRIPTION: SEQ ID NO:2:

```
GAATTCGAGC TCGAGCTTAC TCCCCATCCC CCTGTTGACA ATTAATCATC GGCTCGTATA  60
ATGTGTGGAA TTGTGAGCGG ATAACAATTT CACACAGGAA ACAGGATCCA AGGAAAAACA 120
TATG                                                              124
```

(2) INFORMATION FOR SEQ ID NO:3:
(i) SEQUENCE CHARACTERISTICS:
(A) LENGTH: 151 base pairs
(B) TYPE: nucleic acid
(C) STRANDEDNESS: single
(D) TOPOLOGY: linear
(ii) MOLECULE TYPE: DNA (synthetic)
(iii) HYPOTHETICAL: NO
(iv) ORIGINAL SOURCE:
(A) ORGANISM: *E. coli*
(ix) FEATURE:
(A) NAME/KEY: TRP PROMOTER
(B) LOCATION: 1..151
(D) OTHER INFORMATION: bp 84-89 = "−35"
bp 107-112 = "−10"

(xi) SEQUENCE DESCRIPTION: SEQ ID NO:3:

```
GAATTCAAGG CGCACTCCCG TTCTGGATAA TGTTTTTTGC GCCGACATCA TAACGGTTCT  60
GGCAAATATT CTGAAATGAG CTGTTGACAA TTAATCATCG AACTAGTTAA CTAGTACGCA 120
AGTTCACGTA AAAAGGAGGT ATCGACATAT G                                151
```

(2) INFORMATION FOR SEQ ID NO:4:
(i) SEQUENCE CHARACTERISTICS:
(A) LENGTH: 114 base pairs
(B) TYPE: nucleic acid
(C) STRANDEDNESS: single
(D) TOPOLOGY: linear
(ii) MOLECULE TYPE: DNA (synthetic)
(iii) HYPOTHETICAL: NO
(iv) ANTI-SENSE: NO
(vi) ORIGINAL SOURCE:
(A) ORGANISM: *Pseudonomas aeruginosa*; phage pf3
(ix) FEATURE:
(A) NAME/KEY: P78 PROMOTER
(B) LOCATION: 1..114
(D) OTHER INFORMATION: bp 23-28 = "−35" } or pf3 gene p78 promoter
bp 46-51 = "−10"
bp 100-103 = Shine Dalgarno p78

(xi) SEQUENCE DESCRIPTION: SEQ ID NO:4:

```
GAATTCGATC GCAAAAAAGT ACTTGCAAGT TCCCGAAACC CTGTCTAGAG TTCTAGGTGC  60
ATCTGAATGG AGCTCGGTAC CAATCTGTTT GCTTCCATTG AGGTGCATCA TATG       114
```

(2) INFORMATION FOR SEQ ID NO:5:

-continued

SEQUENCE LISTING (i) SEQUENCE CHARACTERISTICS:
 (A) LENGTH: 105 base pairs
 (B) TYPE: nucleic acid
 (C) STRANDEDNESS: single
 (D) TOPOLOGY: linear
(ii) MOLECULE TYPE: DNA
(iii) HYPOTHETICAL: NO
(iv) ANTI-SENSE: NO
(vi) ORIGINAL SOURCE:
 (A) ORGANISM: *Pseudonomas aeruginosa* and *E. coli*
(ix) FEATURE:
 (A) NAME/KEY: PF3 PROMOTER
 (B) LOCATION: 1..105
 (D) OTHER INFORMATION: bp 23-28 = "−35" } or pf3 gene p78 promoter
 bp 46-51 = "−10"
 bp 92-95 = Shine Dalgarno lac Z gene of *E. coli*
(xi) SEQUENCE DESCRIPTION: SEQ ID NO:5:

| | | | | | | |
|---|---|---|---|---|---|---|
| GAATTCGATC | GCAAAAAAGT | ACTTGCAAGT | TCCCGAAACC | CTGTCTAGAG | TTCTAGGTGC | 60 |
| ATCTGAATGG | AGCTCGGTAC | CCGGGGATCC | AAGGAAAAAC | ATATG | | 105 |

(2) INFORMATION FOR SEQ ID NO:6:
(i) SEQUENCE CHARACTERISTICS:
 (A) LENGTH: 10 amino acids
 (B) TYPE: amino acid
 (C) STRANDEDNESS: single
 (D) TOPOLOGY: linear
(ii) MOLECULE TYPE: peptide
(iii) HYPOTHETICAL: NO
(iv) ANTI-SENSE: NO
(v) FRAGMENT TYPE: internal
(vi) ORIGINAL SOURCE:
 (A) ORGANISM: *Alcaligenes faecalis*
(xi) FEATURE:
 (A) NAME/KEY: DOMAIN, subunit
 (B) LOCATION: 1..10
 (D) OTHER INFORMATION: /note= "aa2=unknown; aa4=unknown; aa9=unknown"
(xi) SEQUENCE DESCRIPTION: SEQ ID NO:6:

| | | | | | | | | | | |
|---|---|---|---|---|---|---|---|---|---|---|
| Gln | Xaa | Gln | Xaa | Val | Glu | Val | Met | Xaa | Thr | 10 |
| 1 | | | | 5 | | | | | 10 | |

(2) INFORMATION FOR SEQ ID NO:7:
(i) SEQUENCE CHARACTERISTICS:
 (A) LENGTH: 11 amino acids
 (B) TYPE: amino acid
 (C) STRANDEDNESS: single
 (D) TOPOLOGY: linear
(ii) MOLECULE TYPE: peptide
(iii) HYPOTHETICAL: NO
(iv) ANTI-SENSE: NO
(v) FRAGMENT TYPE: internal -continued

SEQUENCE LISTING (vi) ORIGINAL SOURCE:
(A) ORGANISM: *Alcaligenes faecalis*
(ix) FEATURE:
(A) NAME/KEY: DOMAIN, subunit
(B) LOCATION: 1..11
(D) OTHER INFORMATION: /note= "aa7=unknown; aa10=unknown"
(xi) SEQUENCE DESCRIPTION: SEQ ID NO:7:

Ser Asn Leu Trp Ser Thr Xaa Pro Glu Xaa Val 11
1 5 10

(2) INFORMATION FOR SEQ ID NO:8:
(i) SEQUENCE CHARACTERISTICS:
(A) LENGTH: 32 base pairs
(B) TYPE: nucleic acid
(C) STRANDEDNESS: single
(D) TOPOLOGY: linear
(ii) MOLECULE TYPE: DNA
(iii) HYPOTHETICAL: NO
(iv) ANTI-SENSE: NO
(vi) ORIGINAL SOURCE:
(A) ORGANISM: *Alcaligenes faecalis*
(ix) FEATURE:
(A) NAME/KEY: OLIGONUCLEOTIDE
(B) LOCATION: 1..32
(D) OTHER INFORMATION: /note= "M: A or C; S: C or G"
(xi) SEQUENCE DESCRIPTION: SEQ ID NO:8:

AGCAACCTGT GGAGCMSCTG CCCGGAGTGC GT 32

PENICILLIN G ACYLASE, A GENE ENCODING THE SAME AND A METHOD FOR THE PRODUCTION OF THIS ENZYME

TECHNICAL FIELD

This invention relates to a gene encoding penicillin G acylase, to penicillin G acylase encoded by this gene and to a method for the production of this enzyme.

BACKGROUND AND RELEVANT LITERATURE

Penicillin G acylase (benzylpenicillin amidohydrolase, also named penicillin amidase; EC 3.5.1.11) is an enzyme used commercially to hydrolyse penicillin G or 3-desacetoxycephalosporin G to phenylacetic acid and 6-aminopenicillanic acid (6-APA) or 7-aminodesacetoxycephalosporanic acid (7-ADCA), respectively, the most important intermediates for the industrial production of semi-synthetic penicillins and cephalosporins. This enzyme also catalyses the reverse reaction, viz. the N-acylation of 6-APA and 7-ADCA with organic esters to generate their corresponding N-acetylated penicillin and 3-cephem compounds, respectively. See the reviews of Vandamme, E.J., In: Microbial Enzymes and Bioconversions, E.H. Rose (Ed.), Economic Microbiology 5, 467–552 (1980); and P.B. Mahajan, Appl. Biochem. Biotechnol. 1, 83–86 (1982).

Various types of microorganisms have been proposed in the literature as Penicillin G acylase producing strains useful for the deacylation of penicillin G and 3-desacetoxycephalosporin G. Examples of such acylase producing microorganisms are certain strains of the species *Escherichia coli, Kluyvera citrophila* and *Proteus rettgeri.* It is to be noted that some penicillin G acylase activity has been described in the whole cell fraction of *Alcaligenes faecalis* (C.A. Claveridge et al., Nature 4733, 237–238 (1960)). However, no enzyme or some enzymes responsible for this activity from *A faecalis* have been described up to now.

The use of recombinant DNA methods has enabled an increase of the production levels of commercially used penicillin G acylases (Mayer et al., Adv. Biotechnol. 1, 83–86 (1982)) and has enlarged the insight into the processing of these enzymes (Schumacher et al., Nucleic Acids Res. 14, 5713–5727 (1986)). The penicillin G acylase of *E. coli* was found to be produced as a large precursor protein, which was further processed into the periplasmic mature protein constituting a small (α) and a large (β) subunit. Cloning and sequencing of the *Kluyvera citrophila* acylase gene has revealed a close harmony with the *E. coli* acylase gene (J.L. Barbero et al., Gene 49, 69–80 (1986)). Also for the *Proteus rettgeri* penicillin G acylase gene a small and a large subunit has been described (G.O. Daumy et al., Gene 49, 69–80 (1986); Spanish patent application No. 8602933).

SUMMARY OF THE INVENTION

In one aspect of the invention a gene is provided encoding penicillin G acylase which has essentially the structure given in FIG. 1. The gene is preferably obtained from *A. faecalis.*

In another aspect of the invention a vector is provided comprising said gene. Also provided is a host system which comprises one or more copies of said gene.

The invention further provides said penicillin G acylase gene under the control of a regulon comprising transcription and/or translation regulating sequences where said regulating sequences are replaced by other transcription and/or translation regulating sequences. These latter regulating sequences may be obtained from the same or another organism.

The present invention further provides a vector comprising this penicillin G acylase gene, manipulated with respect to the regulating sequences as indicated above, and a host comprising said vector. The penicillin G acylase enzyme, resulting from the expression of said gene has a surprisingly good stability and a high specific activity.

In still another aspect of the invention said penicillin G acylase enzyme is provided in isolated form. When used in large scale acylation or deacylation processes it is preferably used in immobilized form.

The present invention further provides a method for producing penicillin G acylase by fermentation of a transformed host encoding said enzyme, and recovery of the penicillin G acylase in isolated form.

These and other embodiments will be outlined below in more detail.

BRIEF DESCRIPTION OF THE SEQUENCE LISTINGS

SEQ ID NO: 1: Nucleotide sequence of the penicillin G acylase gene of *A. faecalis* and derived sequence of amino acids of the new pac enzyme SEQ ID NO: 2: Nucleotide sequence of the tac promoter SEQ ID NO: 3: Nucleotide sequence of the trp promoter SEQ ID NO: 4: Nucleotide sequence of the p78 promoter SEQ ID NO: 5: Nucleotide sequence of the pf3 promoter

SPECIFIC EMBODIMENTS

The new *Alcaligenes faecalis* penicillin G acylase (pac) enzyme can be isolated in a manner known per se: for example, an *A. faecalis* strain is grown in a suitable culture medium, for instance consisting of yeast extract in a buffered solution, particularly in a phosphate buffer at a pH of about 6–8, particularly about 7, optionally in the presence of the inducer KPA. Any *A. faecalis* strain can be used. The enzyme is then purified by a method known per se, preferably in two steps, the first one with for instance an esterified cellulose and subsequently the application of for instance gel chromatography, particularly applying hydroxyapatite.

The purified enzyme can be subjected to amino acid sequence analysis of peptide fragments, preferably the $NH_2$terminus of each of the subunits. From the determined amino acid sequence a DNA probe to detect the gene sequence may be derived. It was established for the first time that the penicillin hydrolyzing activity of *A. faecalis* resides in the purified penicillin acylase, which turns out to be a heterodimer of two subunits of 26 kD and 59 kD in size.

The *A. faecalis* pac gene can be identified from chromosomal DNA in a manner known per se. The gene is essentially of a structure as given in FIG. 1. It is understood that all homologous genes which can hybridize with the sequence depicted in FIG. 1 and which encode an enzyme of essentially the same structure are comprised in this invention. The following equation, which has been derived from analyzing the influence of different factors on hybrid stability: $Tm=81+16.6$ (log10 Ci)+0.4 (% G+C)−600/n−1.5% mismatch (Ausubel et al., supra) where n=length of the shortest chain of the probe Ci=ionic strength (M)

G+C=base composition, can be used to determine which level of homology can be detected using DNA-DNA hybridisation techniques.

Therefore the term "essentially of a structure" is intended to embrace sequences which can include conservative mutations, where the sequence encodes the same amino acid, but which may differ by up to 35% in the DNA sequence according to the above equation, more typically by up to 10%.

A homology comparison of the amino acid sequence of the new *A. faecalis* pac enzyme with the published amino acid sequence of *E. coli* penicillin G acylase (Schumacher et al., supra) revealed an overall homology of only 43%. Furthermore, the homology to the known amino acid sequence of the *Kluyvera citrophila* pac enzyme (Barbero *et al., supra*) is also only 44%.

Figure 4:
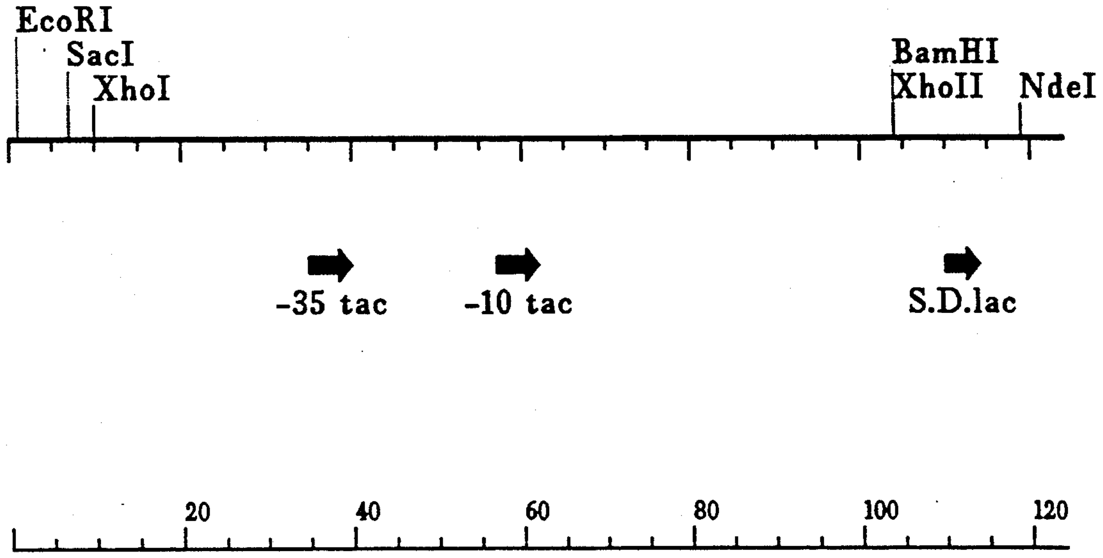
FIG. 4: Structure of the tac promoter.
Figure 5:
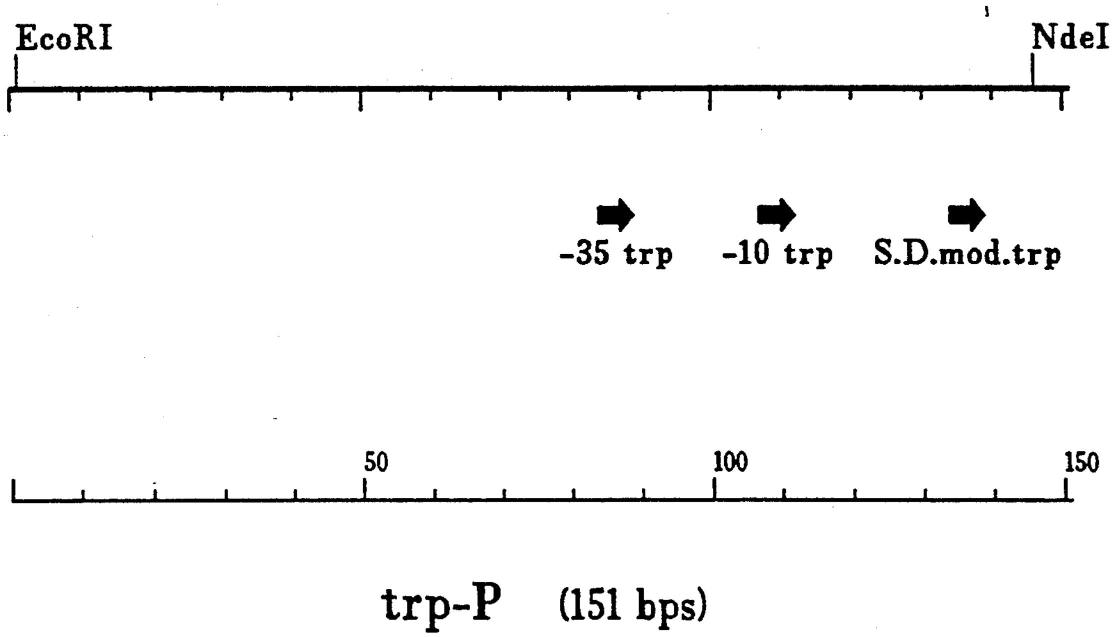
FIG. 5: Structure of the trp promoter.

The *A. faecalis* pac gene can be expressed in *E. coli* under the guidance of its own promoter and/or of the inducible tac or trp promoter (see FIGS. 4 and 5). The results of the penicillin G acylase production are surprisingly good. Using this pac gene with the tac promoter the production is as high as that of the original *A. faecalis* strain, whereas in the latter case potassium phenylacetate needs to be used as an inducer. The *E. coli* strain with the *A. faecalis* pac gene under the control of the trp promoter shows —without any induction—a penicillin G acylase production which is as much as five times higher than that of the strains mentioned above. In both strains the dependence on induction using a potassium phenylacetate inducer, which is expensive, can now be avoided.

In order to obtain a production strain with only homologous DNA, transformation into *A. faecalis* itself was developed. Successful DNA transformation into *A. faecalis* can be suitably achieved by two different methods. First of all, conjugational transfer of broad-host range plasmids from *E. coli* to *A. faecalis* can be obtained. Secondly, electroporation of *A. faecalis* with plasmids based on replicon RSF 1010 can be used (BIORAD-gene pulser).

Upon cloning of the *A. faecalis* gene different transcription sequences can be used. Firstly, the *A. faecalis* pac gene can be cloned in *A. faecalis* under the control of its own promoter. The production of penicillin G acylase is highly improved compared with the *A. faecalis* strain without extra pac gene(s) and scarcely dependent on potassium phenylacetate induction. Secondly, the use of the *E. coli* trp promoter, independently of any inducer, leads to a similarly high amount of penicillin G acylase being obtained. Thirdly, by the application of two expression elements derived from *Pseudomonas aeruoinosa* phage pf3, promoters pf3 and p78, (Luiten, PhD thesis, Nijmegen (1986)) the production of penicillin G acylase is somewhat lower than that achieved with an *A. faecalis* strain with extra pac gene(s) under the control of its own or *E. coli* tro promoter, but is still improved compared to the *A. faecalis* strain without extra pac gene(s) and is much less dependent on potassium phenylacetate induction.

The prior art does not teach the use of *A. faecalis* to produce penicillin G acylase in isolated form. Also neither the improved properties of the new *A. faecalis* penicillin G acylase enzyme related to that of *E. coli* nor the use of recombinant DNA methods to increase and facilitate the production of penicillin G acylase from *A. faecalis* have been suggested in the prior art up to now.

Penicillin G acylase, produced with the aid of the *A. faecalis* pac gene, cloned particularly in a gram-negative microorganism, preferably in an *Alcaligenes* or *Escherichia* microorganism, more preferably in *A. faecalis,* is produced in surprisingly large amounts. Furthermore, the stability and especially the specific activity of the penicillin G acylase gene is much greater than that of the penicillin acylases known sofar.

A purified preparation of *A. faecalis* is also provided, showing a higher specific activity of this enzyme on the preferred substrate penicillin G than any of the presently known penicillin acylases. Furthermore the purified preparation is used to determine the thermostability of *A. faecalis* penicillin G acylase in comparison to *E. coli* penicillin acylase. The stability of *A. faecalis* penicillin G acylase is significantly better than that of *E. coli* penicillin G acylase, allowing a prolonged use under industrial conditions.

Preferably, in industrial processes penicillin G acylase, and also that provided by the present invention, is used in immobilized form. The carrier on which it is immobilized typically comprises gelatin optionally crosslinked with chitosan, aluminum oxide, silicium oxide, ion exchange resins or acrylate beads, such as, for instance, Eupergit ©.

The following examples will further illustrate the present invention.

MATERIALS AND METHODS

Cloning and Detection of Acylase Genes

General cloning techniques were performed as described by Maniatis et al. (1982 and 1989, Molecular Cloning, Cold Spring Harbor Laboratory) or Ausubel et al. (1987, Current Protocols in Molecular Biology, John Wiley and Sons Inc., New York) or B. Perbal (1988, A Practical Guide to Molecular Cloning, 2nd edition, John Wiley and Sons Inc., New York). These handbooks describe in detail the protocols for construction and propagation of rDNA molecules, the procedures for making gene libraries and the protocols for mutating DNA in a site directed or random fashion. Enzymes used for DNA manipulations were purchased from and used according to instructions from commercial suppliers. Plasmids and *E. coli* cloning hosts were obtained from public culture collections as the Phabagen Collection (Utrecht).

Media

Selective media for phenylacetyl L-leucine (fal) were prepared as described (Garcia et al., ibid). Minimal plates are as follows: M63 minimal agar, 2 g/l glucose, 1 mg/l thiamine, 10 mg/l L-proline and the appropriate antibiotic (50 μg/ml chloramphenicol (cap) or 25 μg/ml ampicillin (amp)). Transformants of *E. coli* HB101 (Leu−) growing exclusively in the presence of the acyl L-leucine are considered to harbor an acylase gene.

Minimal E* medium: 16 g/l Difco agar, spore elements 0.2 g/l $MgSO_4 \cdot 7H_2O$, 10 g/l $KH_2PO_4$, 3.5 g/l $Na(NH_4)HPO_4$, 1.6 g/l sodium citrate.

4xLBC medium: Yeast extract 20 g/l, bactotryptone 40 g/l, NaCl 10 g/l, casaminoacids 4 g/l, basildon 0.25 g/l (antifoam 86-103Basildon Chemical Corporation), pH 7.0.

AF (*Alcaligenes faecalis*) medium: Yeast extract 15 g/l, $Na_2HPO_4.2H_2O$ 4.5 g/l, $KH_2PO_4$ 3.4 g/l, pH 7.0 (in case of induction: potassium phenylacetic acid (KPA) 1.0 g/l)

2xTY medium: 16 g/l bacto tryptone, 10 g/l yeast extract, 5 g/l NaCl.

Phenylacetyl leucine was purchased from LGSS, Transferbureau Nijmegen.

The *A. faecalis* strain ATCC 19018 (also deposited as NCTC 415) was used as a donor strain for the *A. faecalis* pac gene, and as a host for recombinant plasmids.

*E. coli* strains JM101, WK6 and HB101 (Phabagen, Utrecht) were used as hosts for recombinant plasmids.

EXAMPLE 1

Purification and Characterization of *A. Faecalis* Penicillin Acylase

Strain *A. faecalis* ATCC 19018 was grown in a AF medium. Cells were harvested by centrifugation and resuspended in the following buffer: Tris 0.1 M pH 8.0; EDTA 0.2 mM; lysozyme 0.02 mg/ml and incubated for 2 hours at 30° C. Cell debris was removed by centrifugation.

The penicillin G acylase (pac) was purified in two steps. The first one was obtained with carboxymethyl cellulose (CM-52 Whatman). The second one consisted in the elimination of the remaining contaminating proteins through a hydroxyapatite gel chromatography (Biogel HTP from Biorad). The resulting pure pac was shown to be composed of two nonidentical subunits. The small (α) and large (β) subunit were subjected to $NH_2$ terminal amino acid analysis. The result was as follows:

subunit α (26 KDa) (SEQ ID NO: 6) $NH_2$—Q—X—Q—X—V—E—V—M—X—T subunit β (59 KDa) (SEQ ID NO: 7) $NH_2$—S—N—L—W—S—T—X—P—E—X—V

EXAMPLE 2

Cloning of the *A. Faecalis* Penicillin Acylase Gene

Figure 1:
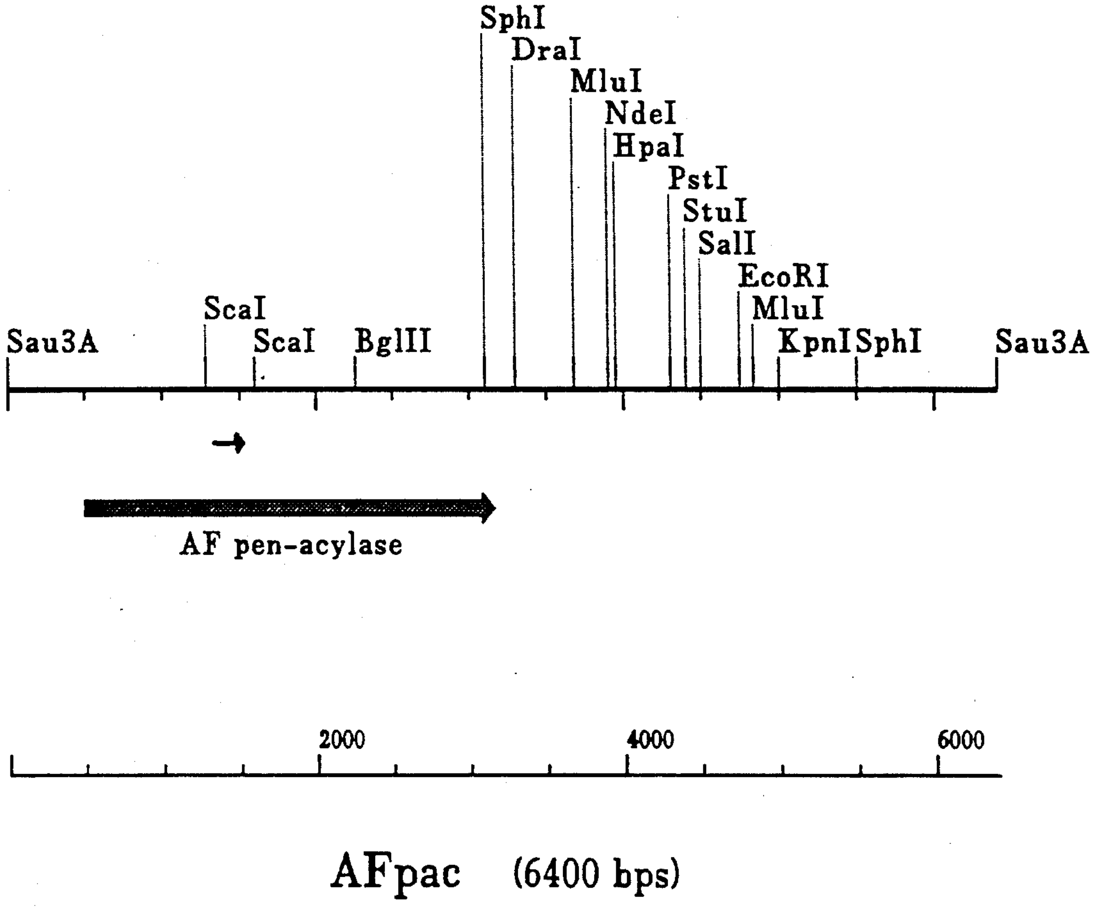
FIG. 1: Physical map of the *A. faecalis* penicillin G acylase gene region. The insert of pAF*1* has been depicted.

Chromosomal DNA of *A. faecalis* (ATCC 19018) was isolated and partially digested with Sau3A. Fractions ranging from 4 kb to 7 kb were purified and ligated into vector pACY184, which was digested with BamHI. DNA was transformed into *E. coli* HB101 and plated onto fal-plates (see methods). Two positive clones pAFI and pAF2 could be identified. These clones were also tested with positive result in the Serratia marcescens overlay technique (Meevootisom, V. et al., Appl. Microbiol. Biotechnol. 25, 372-378 (1987)). The 6.4 kb insert of the pAF1 plasmid is shown in FIG. 1. The localization of the gene was determined with the aid of an oligonucleotide designed on the NH2 terminal sequence of the β-subunit of *A. faecalis* pac.

The following oligonucleotide was used as a hybridisation probe on the pAF1 insert (SEQ ID NO: 8):

AGC AAC CTG TGG AGC A/C C/G C TGC CCG GAG TGC GT

From the position of the hybridising signal on the restriction map the orientation of the *A. faecalis* pac gene was determined (FIG. 1).

EXAMPLE 3

Determination of the Sequence of *A. Faecalis* Penicillin Acylase

The 3.9 kb Sau3A-NdeI subclone of the 6.4 kb insert, was shown to give pac activity, whereas the 3.1 kb Sau3A-Sph1 fragment was inactive (FIG. 1). The DNA sequence of the 3.9 kb insert was determined by deoxy sequencing of suitable fragments in pTZ18R and pTZ19R (Pharmacia). The encoding DNA sequence and the derived amino acid sequence for *A. faecalis* pac is shown in SEQ ID NO: 1. From the derived amino acid sequence it can be concluded that *A. faecalis* pac is encoded as a large single polypeptide chain which undergoes processing into two different subunits named α and β. At the 5′ site of the precursor a typical signal sequence responsible for the translocation of the enzyme into the periplasm is shown.

EXAMPLE 4

Expression of Penicillin Acylase in *E. Coli*

Figure 2:
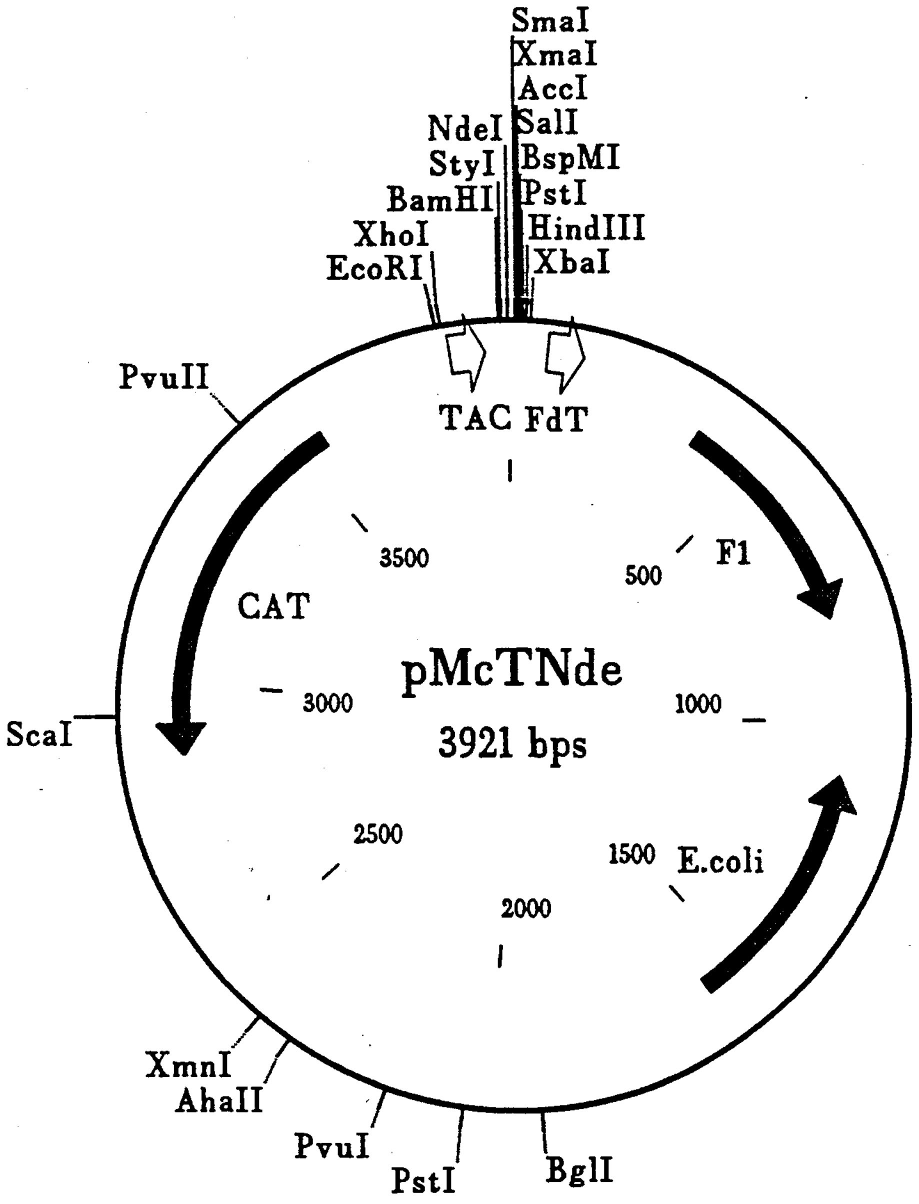
FIG. 2: Structure of the plasmid pMcTNde.
Figure 3:
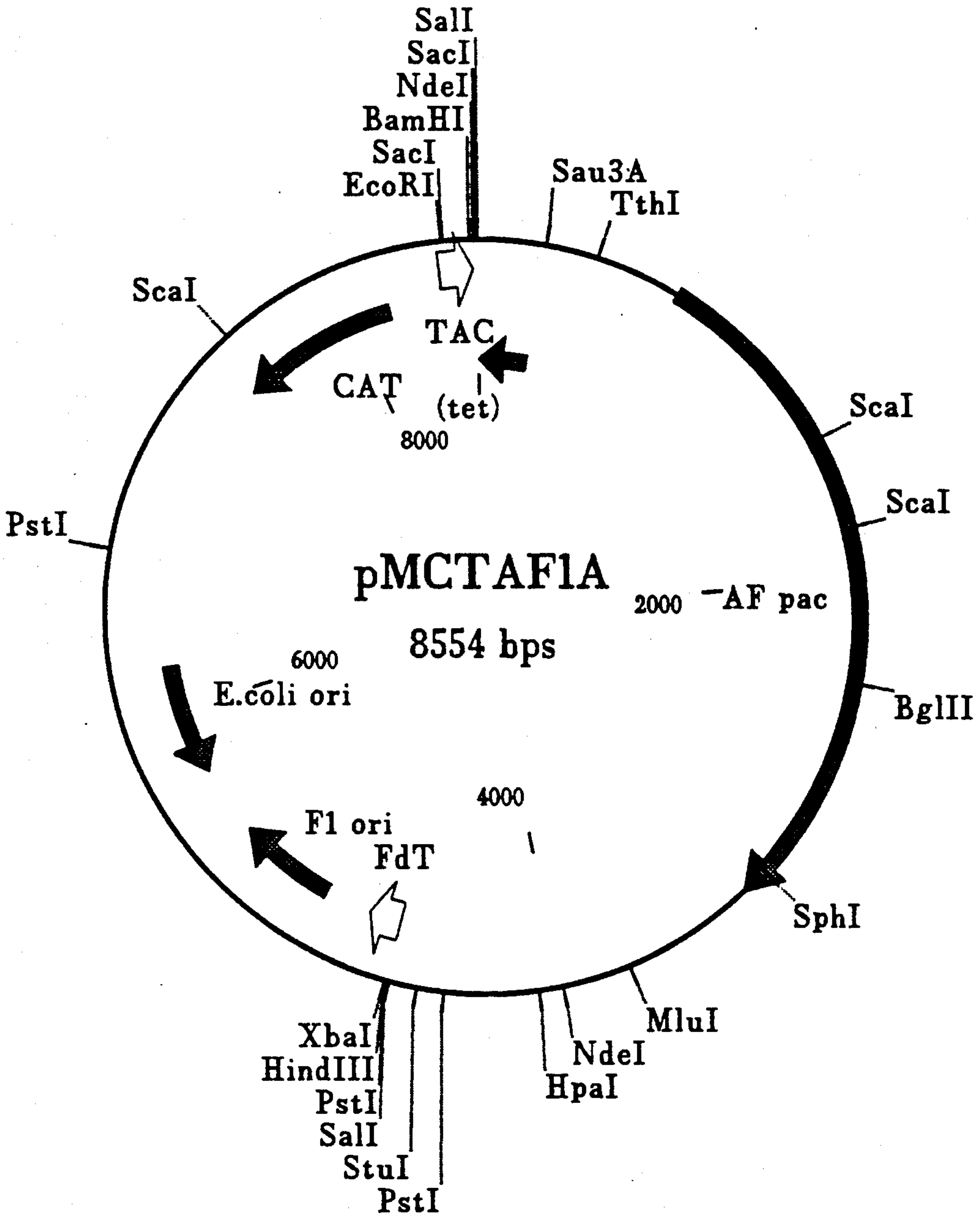
FIG. 3: Structure of the plasmid pMCTAF*1*A.

Plasmid pAF1 was digested with SalI and a 4.8 kb fragment was purified. The fragment was ligated into SalI linearized vector pMCT-Nde. The latter vector was constructed from plasmid pMc5-8 (EP-A-0351029) by insertion of a fragment containing the tac promoter followed by a RBS site and a NdeI cloning site (FIG. 2). The resulting plasmid pMcTAFIA (FIG. 3) obtained after transformation into *E. coli* HB101 expresses pac under guidance of its own promoter and/or of the inducible tac promoter (De Boer et al., Proc. Natl. Acad. Sci., 80, 21 (1983)).

In order to further improve the expression level of pac two strong *E. coli* promoters were cloned in a precise fusion to the acylase startcodon. To do this an NdeI site was constructed at the ATG startcodon using oligonucleotide site directed mutagenesis (Stanssens et al., 1989) of plasmid pMcTAF1A resulting in plasmid pMcTAF1ANde. This plasmid was digested with NdeI and recircularized resulting in the correct positioning of the tac promoter in front of the acylase gene (plasmid pMcAFtac). In order to insert another promoter plasmid pMcTAF1Nde was digested with EcoRI and NdeI and the large fragment was purified on agarose gel. The tryptophan promoter fragments were inserted into this purified EcoRI-NdeI fragment of pMcTAF1ANde using 6 synthetic oligonucleotides.

The DNA sequences of these promoters are depicted in SEQ ID NO: 2 and 3, respectively, and the structures of these promoters in FIGS. 4 and 5, respectively.

These promoter constructs were transformed into *E. coli* HB101 and tested for expression of pac. Table 1 shows the results as compared to the expression level of *A. faecalis* ATCC 19018. Induction of the tac promoter with isopropylthio-β-galactoside (IPTG) and the trp promoter with indol acrylic acid (IAA) was also tested.

TABLE 1

| | Expression of pac in *E. coli* | | | |
|---|---|---|---|---|
| Strain | KPA | IAA | IPTG | PAC units* |
| *A. faecalis* ATCC 19018 | − | − | − | 0.1 |
| *A. faecalis* ATCC 19018 | + | − | − | 1 |
| pMcAFtac | − | − | − | 1 |
| pMcAFtac | − | − | + | 17 |
| pMcAFtrp | − | − | − | 4 |
| pMcAFtrp | − | + | − | 5 |

*relative units with *A. faecalis* Atcc 19018 in the medium with KPA standarized as 1.0

*E. coli* HB101 containing various plasmids was grown in 4XLBC for 24 hours. *A. faecalis* was grown in AF medium for 24 hours.

EXAMPLE 5

Expression of Penicillin Acylase in *A. Faecalis*

In order to enable stable transfer of qenetic information into *A. faecalis* a DNA transformation system and a stable cloning vector had to be researched. Surprisingly it was found that triparental mating of plasmid pKT248 (Bagdasarian et al., Gene 16, 237-247 (1981)) into *A. faecalis* was possible by applying a technique as described (Friedman et al., Gene 18, 289-296 (1982)) with the following modifications:

*E. coli* MC1061 carrying helper plasmid pRK2013 (Figurski & Helinski, Proc. Natl. Acad. Sci. 76, 1648 (1979)) is mixed with *E. coli* HB101 (pKT248) and *A. faecalis* recipient strain on 2xTY agar plates.

Plates are incubated at 30° C. overnight to allow conjugation to take place.

The conjugation plates are replicated to selective agar plates containing minimal E* medium including citrate, spore elements and the selective antibiotics step (50 μg/ml) and cap (25 μg/ml). Incubation at 30° C. overnight is performed. Due to auxotrophic markers the *E. coli* strains are counter-selected for. The *A. faecalis* colonies are subsequently spread on 2xTY plates containing 300 μl/ml streptomycine.

Figure 6:
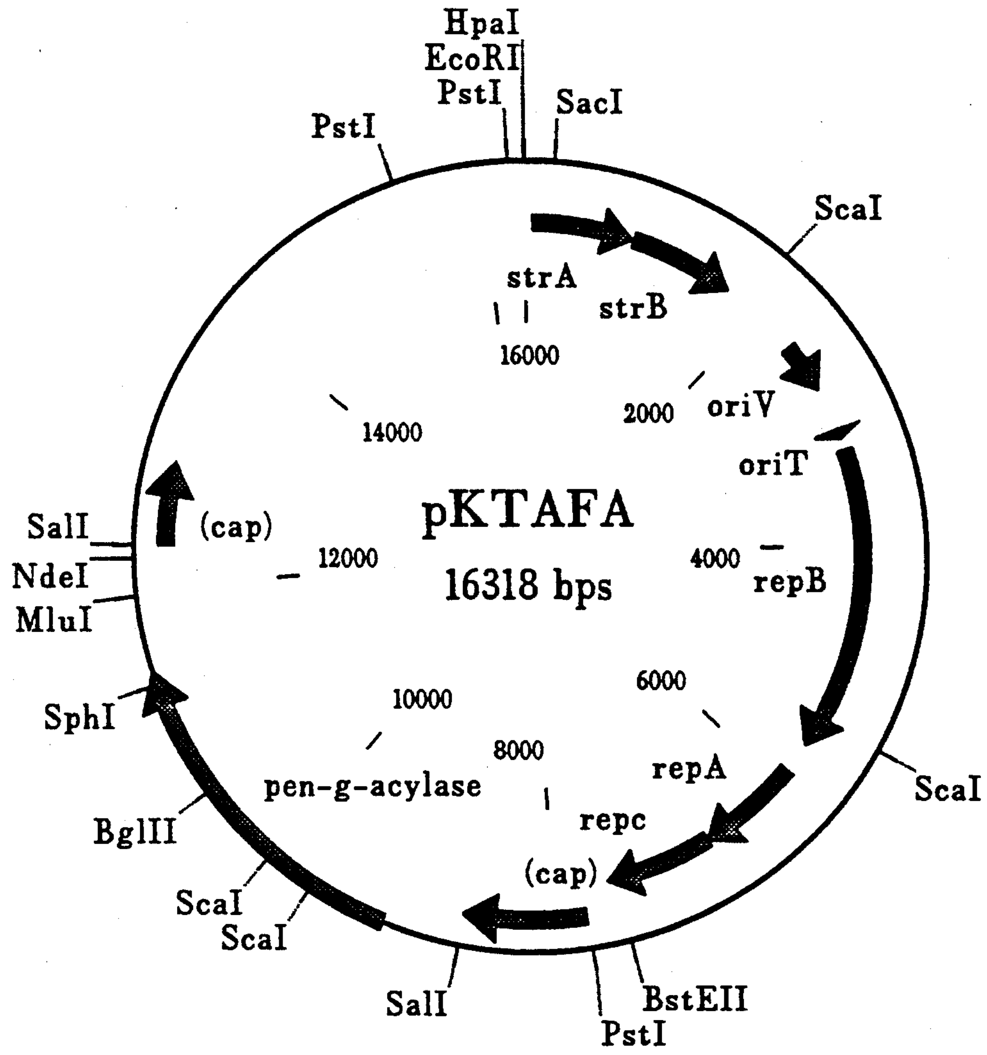
FIG. 6: Structure of the plasmid pKTAFA.

Subcloning of the *A. faecalis* pac gene was done into the unique SalI site of plasmid pKT248. The TthIII-HpaI fragment of plasmid pAFI was isolated and filled in with Klenov polymerase. The SalI site of linearized pKT248 was also made blunt end and plasmid pKTAFA (FIG. 6) was obtained after transformation into *E. coli* HB101 and selection on fal plates. After isolation this plasmid was transferred into *A. faecalis* using the triparental mating technique as described above. The strain obtained was grown in shake flasks with *A, faecalis* growth medium and compound to the original strain. As can be seen in Table 2 the production of pac in the strain with pKTAFA is highly improved. Furthermore it can be seen that even in absence of the inducer KPA a high production can be obtained. This allows the omission of the expensive inducer KPA from industrial fermentation media.

In order to test heterologous promoters in front of the pac gene the EcoRI-SalI fragment of pMcAFtrp, pMcAFpf3 and pMcAFp78, respectively, were subcloned into EcoRI, SalI linearized vector pJRD215 (Davison et al., Gene 51, 275-280 (1987)). All three promoter constructions were obtained in *E. coli* HB101 as pJRDAFtrp, pJRDAFpf3 and pJRDAFp78 and subsequently transferred into *A. faecalis* ATCC 19018. Expression of pac from these plasmids was tested in the presence or absence of KPA (Table 2).

TABLE 2

| Production of pac in *A. faecalis* transformants | | | |
|---|---|---|---|
| Strain | KPA | IAA | PAC units* |
| pKT248 | − | − | 0.1 |
| pKT248 | + | − | 1 |
| pKTAFA | − | − | 18 |
| pKTAFA | + | − | 22 |
| pJRDAFtrp | − | − | 18 |
| pJRDAFtrp | − | + | 19 |
| pJRDAFpf3 | − | − | 5 |
| pJRDAFpf3 | + | − | 8 |
| pJRDAFp78 | − | − | 3 |
| pJRDAFp78 | + | − | 5 |

*relative units with *A. faecalis* ATCC 19018 in the medium with KPA standarized as 1.0

Figure 7:
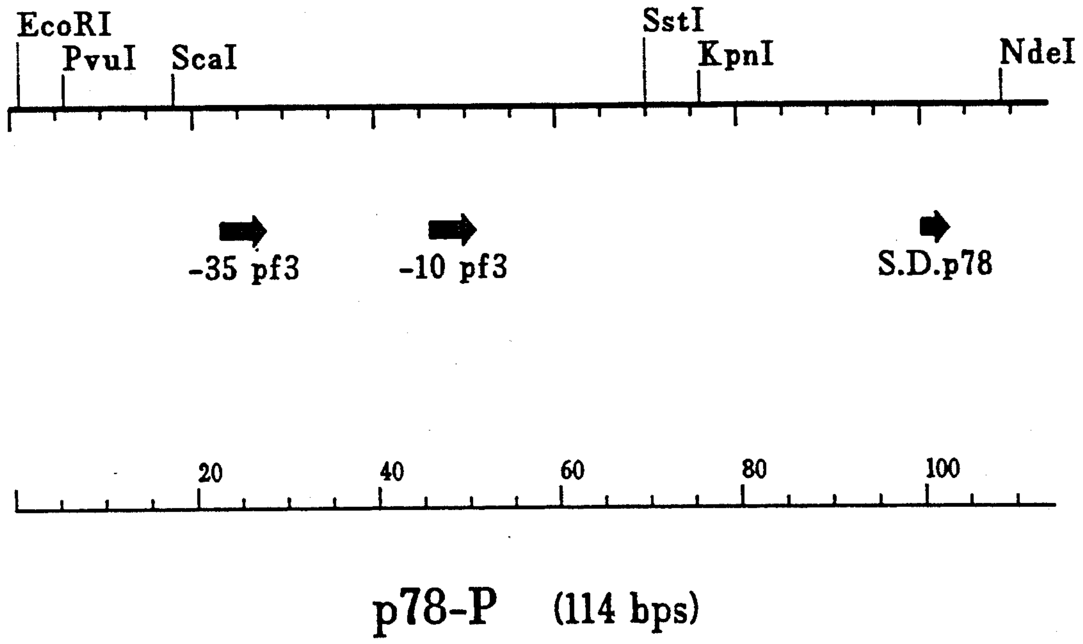
FIG. 7: Structure of the p78 promoter.
Figure 8:
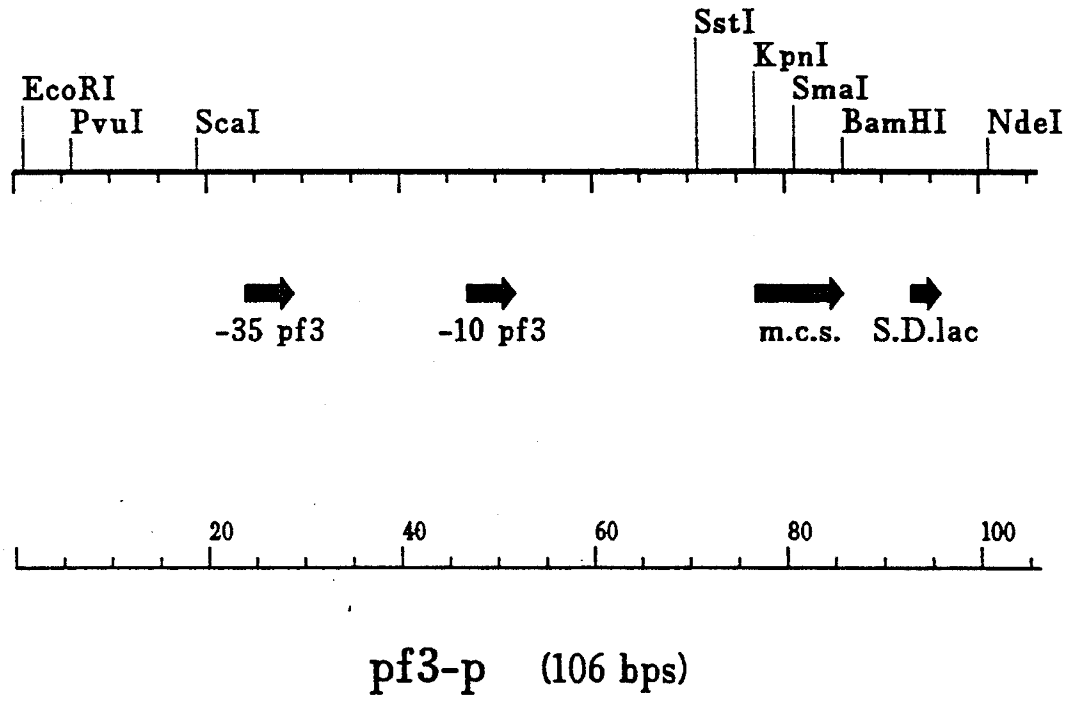
FIG. 8: Structure of the pf3 promoter.

All plasmids were transferred via triparental mating to *A. faecalis* ATCC 19018. The promoters p78 and pf3 are selected from phage pf3 (Luiten, supra). The DNA sequences of these promoters are depicted in Sequence listings 4 and 5, respectively, and the structures of these promoters in FIGS. 7 and 8, respectively.

EXAMPLE 6

Stability of *A. Faecalis* Penicillin Acylase

*A. faecalis* penacylase and *E. coli* were tested for thermostability using the following protocol: Enzyme solutions are incubated at various temperatures for 5 minutes in a solution of 100 mM sodium phosphate, pH 7.5. Residual activity was measured at 35° C. with 50 mM penicillin G as substrate. The temperatures with 100%, 50% and 0% residual activity after 5 minutes were determined. From Table 2 it can be concluded that the *A. faecalis* enzyme is significantly more stable than the *E. coli* enzyme.

| | 100% | 50% | 0% |
|---|---|---|---|
| *A. faecalis* | 45° C. | 58.0° C. | 66° C. |
| *E. coli* 5K | 40° C. | 54.8° C. | 60° C. |

The enzyme preparation *E. coli* 5K was obtained from Produktions Gesellschaft fur Biotechnologie Braunschweig (Mayer et al., supra).

I claim:

1. A isolated gene encoding penicillin G acylase having essentially the nucleotide sequence depicted in SEQ ID NO: 1.

2. A gene according to claim 1 which is isolated from *Alcaligenes faecalis.*

3. A gene according to claim 1 or 2 under the control of a regulon comprising transcription and/or translation regulating sequences, wherein one or both of said regulating sequences have been replaced by other transcription and/or translation regulating sequences, respectively, obtained from the same or another organism.

4. A cloning vector comprising one or more penicillin G acylase genes as defined in claim 1, 2 or 3.

5. A vector according to claim 4, wherein the transcription sequences of the penicillin G acylase gene are replaced by the trp promoter.

6. A prokaryotic transformed host comprising a vector as defined in claim 4 or 5.

7. A transformed host according to claim 6 which is a gram-negative microorganism.

8. A transformed host according to claim 7 wherein the microorganism is of the genus Alcaligenes or Escherichia.

9. A transformed host according to claim 8 wherein the microorganism is *Alcaligenes faecalis.*

10. A method of preparing penicillin G acylase which comprises culturing a transformed host as claimed in any one of the claims 6 to 9 and recovering the penicillin G acylase in isolated form.

11. A method for producing, or enhancing the production of, penicillin G acylase in a prokaryotic host, the method comprising (i) preparing a DNA vector as defined in claim 4 or 5; (ii) transforming the host with the said vector; and (iii) cloning the resulting transformants and selecting the same.

12. A method according to claim 11, characterized by transforming a gram-negative microorganism.

13. A method according to claim 12, characterized by transforming a microorganism of the genus Alcaligenes or Escherichia.

14. A method according to claim 13, characterized by transforming *Alcaligenes faecalis.*

* * * * *